United States Patent [19]
Blank et al.

[11] Patent Number: 4,767,789
[45] Date of Patent: * Aug. 30, 1988

[54] SPRAY DRIED ACETAMINOPHEN

[75] Inventors: Robert G. Blank, Vineland; Dhiraj S. Mody, Hammonton; Gary R. Agism, Cherry Hill Camden; Richard J. Kenny, Sommerset, all of N.J.

[73] Assignee: American Home Products Corporation (Del.), New York, N.Y.

[*] Notice: The portion of the term of this patent subsequent to Jul. 26, 2005 has been disclaimed.

[21] Appl. No.: 921,556

[22] Filed: Oct. 21, 1986

[51] Int. Cl.$^4$ .............................................. A61K 31/74
[52] U.S. Cl. .................................. 514/629; 424/464; 424/499; 514/974
[58] Field of Search ................. 514/629; 424/464, 499

[56] References Cited

U.S. PATENT DOCUMENTS 4,439,453  3/1984  Vogel .................................. 514/629
4,631,284  12/1986  Salpekar et al. ..................... 514/629

FOREIGN PATENT DOCUMENTS 58-172311  10/1983  Japan .

Primary Examiner—Joseph L. Schofer
Assistant Examiner—Peter F. Kulkosky
Attorney, Agent, or Firm—John W. Routh

[57] ABSTRACT

A therapeutic taste-neutral powder form of acetaminophen obtained by spray-drying a suspension of acetaminophen in a solution of ethylcellulose in an organic solvent selective for ethylcellulose.

6 Claims, No Drawings

SPRAY DRIED ACETAMINOPHEN

BACKGROUND OF THE INVENTION

1. Field of the Invention

This invention relates to a novel therapeutic form of spray dried acetaminophen having a neutral taste which can be formulated into for example, fast dissolving dosage forms as described in U.S. Pat. Nos. 4,305,502 and 4,371,516. More specifically this invention relates to a taste neutral spray dried powder formed by spray drying a suspension of acetaminophen in a solution of ethylcellulose in, for example, methylene chloride. By taste-neutral it is meant that the powder has essentially no taste and is not sweet nor bitter.

2. Prior Art

Acetaminophen, a widely used analgesic and antipyretic, is not palatable enough to be used in chew-type tablets for those people who do not swallow whole solid-type dosage forms.

The use of flavor agents eg. chocolate, banana, orange, lemon, licorice, root beer, and raspberry, in particular, have been proposed for bitter tasting drugs. These agents are not dependable masking ingredients. Mint flavors can be useful in ameliorating a chalky taste parameter. Bitter properties, however, are very difficult to mask to any great extent, particularly, when they do not mimic the expected natural taste of the flavor agent.

Other properties including mouthfeel also need to be addressed in consideration of the oral acceptance of chewable or chew-type tablets.

The fast dissolving dosage forms described in U.S. Pat. Nos. 4,305,502 and 4,371,516 are manufactured to disintegrate in water within five seconds or less and hence dissolve rapidly in the saliva of the mouth. Heretofore the use of such dosage forms was restricted to pharmaceuticals which had a neutral taste or a slightly disagreeable taste which could be masked by a flavoring agent. Pharmaceuticals with a bitter taste such as acetaminophen and ibuprofen, however, could not heretofore be used in such dosage forms.

Summary of the Invention

According to this invention, a novel therapeutic taste-neutral powder form of spray-dried acetaminophen is provided which can be formulated into fast dissolving dosage forms, chewable tablets and the like. The powder is formed by spray drying a solution having dissolved therein ethyl cellulose, the solution having finely divided acetaminophen suspended therein and a solids content of at least about 14% by weight, and the solvent being an organic solvent selective for ethylcellulose.

According to another aspect of this invention, a pharmaceutical dosage form for oral administration as a solid is provided, which dosage form can be disintegrated by water at 37° C. within ten seconds, and comprises as the pharmaceutical agent incorporated therein the taste neutral powder form of spray dried acetaminophen of this invention.

Details of the Invention

The acetaminophen useful in this invention is the pharmaceutical grade. The ethyl cellulose useful in this invention is also National Formulary or pharmaceutical grade. Suitable grades are the ETHOCEL brand marketed by Dow Chemical Company, Midland Mich. and that marketed by Hercules, Inc. of Wilmington, Del.

The weight percent of acetaminophen in the taste neutral powder can be from about 60 to 76% by weight and the weight percent of the ethylcellulose can range from 24% to 40% by weight. At 25% by weight of ethylcellulose, there is a slightly bitter taste but at 26% and above the powder is taste neutral.

The solvent for the ethylcellulose can be, for example, methylene chloride, but must be an organic solvent selective for the ethylcellulose and in which the acetaminophen is not soluble. By not soluble is meant a solvent in which acetaminophen is not soluble to any appreciable extent. The solids content of the solution of ethyl cellulose having acetaminophen suspended therein is within the range of about 14 to about 19% by weight.

Spray dryers can be of the usual laboratory or commercial type. Suitable spray dryers are manufactured by Buchi Laboratoriums-Technik AG, by the Anhydro Company of Attleboro, Mass. and by Niro Atomizer Inc., of Columbia, Md.

The spray dryer employed in the following examples was a Niro Portable Spray Dryer, Model No. 21231-0001. The operating conditions include a variable air inlet temperature, a variable outlet temperature, a variable air pressure of compressed air driving the atomizer wheel, and a variable feed rate.

The following examples illustrate the formation of the taste-neutral spray dried acetaminophen powder of the invention. In these examples, the ethyl cellulose was obtained from the Dow Chemical Company, Midland, Mich. It was a dry material of the standard type having a viscosity designation of 10 and an ethoxy content of 48.0% to 49.5%. The acetaminophen was USP grade and was pre-screened through 20 mesh (Tyler).

EXAMPLE 1

In this example, the feed mixture to the spray dryer was composed of the following materials.

| Ingredient | Weight % Ingredient in Suspension | Weight % Solids in powder | Grams Ingredient in 1000 grams suspension |
| --- | --- | --- | --- |
| Acetaminophen, USP | 14.00 | 73.68 | 140 |
| Ethyl Cellulose, NF | 5.00 | 26.32 | 50 |
| Methylene Chloride | 81.00 | — | 810 |
| Total: | 100.00 | 100 | 1000 g. |

The ethyl cellulose was dissolved in the methylene chloride contained in a stainless steel mixing vessel with the aid of a Lightnin mixer. The acetaminophen was then dispersed with mixing and transferred to the feed tank of the Niro Portable Spray Dryer.

The spray dryer was operated with a feed rate of 67 grams per minute and the air inlet heater was set to produce an air outlet temperature of 25°–30° C. The air pressure was 4.8 bar.

The product from the spray dryer was a fine, white powder and, when tasted, was tasteless and produced no bitterness characteristic of acetaminophen.

EXAMPLE 2

In this example, the solids content of the suspension was decreased as follows:

| Ingredient | Weight % Ingredient in Suspension | Weight % solids in powder | Grams Ingredient in 2000 grams suspension |
| --- | --- | --- | --- |
| Acetaminophen | 7.00 | 73.68 | 140 |
| Ethyl Cellulose, NF | 2.50 | 26.32 | 50 |
| Methylene Chloride | 90.50 | — | 1810 |
| Total: | 100.00 | 100.00 | 2000.0 g. |

The spray dryer was operated with a feed rate of 57 grams per minute with an air pressure of 4.6 bar. The air inlet heater was set so as to produce an air outlet temperature of 25° to 30° C.

The product from the spray dryer was a flowable, fine white powder and, when tasted produced a bitter taste. This result was most probably due to the low solids content of the feed to the spray dryer, which solids content must be above about 14% by weight.

EXAMPLE 3

In this example, the feed mixture to the spray dryer was composed of the following materials and the mixing procedure was the same as in Example 1.

| Ingredient | Weight % Ingredient in Suspension | Weight % Solids in powder | Grams Ingredient in 1000 grams suspension |
| --- | --- | --- | --- |
| Acetaminophen | 14 | 73.68 | 140 |
| Ethyl Cellulose, NF | 5 | 26.32 | 50 |
| Methylene Chloride | 81 | — | 810 |
| Total: | 100.00 | 100 | 1000 grams |

The spray dryer was operated with a feed rate of 32 grams per minute and the air inlet heater was set to produce an air outlet temperature of 25°–30° C. The air pressure was 4.6 bar.

The product was a flowable, fine, white powder that, when tasted, was tasteless with no bitter taste characteristic of acetaminophen.

EXAMPLE 4

In this example, the feed mixture to the spray dryer was composed of the following materials and the mixing procedure was the same as in Example 1.

| Ingredient | Weight % Ingredient in Suspension | Weight % Solids in powder | Grams Ingredient in 1000 grams suspension |
| --- | --- | --- | --- |
| Acetaminophen | 10.50 | 73.68 | 105.0 |
| Ethyl Cellulose, NF | 3.75 | 26.32 | 37.5 |
| Methylene Chloride | 85.75 | — | 857.5 |
| Total: | 100.00 | 100 | 1000 grams |

The spray dryer was operated with a feed rate of 21 grams per minute and the air inlet heater was set to produce an air outlet temperature of 25°–30° C. The air pressure was 4.6 bar.

The product, when tasted, was practically tastless and produced a very, very, slightly bitter aftertaste.

EXAMPLE 5

In this example, the feed mixture to the spray dryer was composed of the following materials and the mixing procedure was the same as in Example 1 except that the dibutyl sebacate was added after the ethyl cellulose.

| Ingredient | Weight % Ingredient in Suspension | Weight % Solids in powder | Grams Ingredient in 1000 grams suspension |
| --- | --- | --- | --- |
| Acetaminophen | 10.50 | 71.77 | 105.00 |
| UNIFLEX brand of Dibutyl Sebacate | 0.38 | 2.60 | 3.80 |
| Ethyl Cellulose, NF | 3.75 | 25.63 | 37.50 |
| Methylene Chloride | 85.75 | — | 853.70 |
| Total: | 100.00 | 100 | 1000 grams |

The spray dryer was operated with a feed rate of 28.16 grams per minute and the air inlet heater was set to produce an air outlet temperature of 25°–30° C. The air pressure was 4.8 bar.

The yield of spray dried powder was 81%, 61 grams from the cyclone and 40 grams from the chamber. The product was a fine white, free-flowing powder.

The product, when tasted, produced a very, very slightly bitter taste characteristic of acetaminophen.

EXAMPLE 6

In this example, the feed mixture to the spray dryer was composed of the following materials.

| Ingredient | Weight % Ingredient in Suspension | Weight % Solids in powder | Grams Ingredient in 1000 grams suspension |
| --- | --- | --- | --- |
| Acetaminophen | 10.50 | 71.00 | 105.00 |
| UNIFLEX brand of Dibutyl Sebacate | 0.38 | 2.57 | 3.80 |
| Ethyl Cellulose, NF | 3.75 | 25.35 | 37.5 |
| Colloidal Silica | 0.16 | 1.08 | 1.6 |
| Methylene Chloride | 85.21 | — | 852.1 |
| Total: | 100.00 | 100 | 1000 grams |

The procedure for this example was essentially that of Example 5, except that the colloidal silica was added after the dibutlyl sebacate. The colloidal silica used in this example has a particle size of about 10 millimicrons and is marketed as Cabosil-M-5 by Cabot Corporation of Boston, Mass.

The sprayer dryer was operated with a feed rate of 35.4 grams per minute and the air inlet heater was set to produce an air outlet temperature of 25°–30° C. The air pressure was 4.8 bar.

The yield of spray dried powder was 78%, 74.8 grams from the cyclone and 32 grams from the chamber. The product was a fine white, free-flowing powder.

The product, when tasted, was taste-neutral and produced a very, very slightly bitter aftertaste characteristic of acetaminophen.

EXAMPLE 7

In this example, the feed mixture to the spray dryer was composed of the following materials.

| Ingredient | Weight % Ingredient in Suspension | Weight % Solids in powder | Grams Ingredient in 1000 grams suspension |
|---|---|---|---|
| Acetaminophen | 10.50 | 70.00 | 105.00 |
| UNIFLEX brand of Dibutyl Sebacate | 0.38 | 2.54 | 3.80 |
| Ethyl Cellulose, NF | 3.82 | 25.46 | 38.20 |
| Colloidal Silica | 0.15 | 1.00 | 1.50 |
| NUTRASWEET brand of Aspartame | 0.15 | 1.00 | 1.50 |
| Methylene Chloride | 85.00 | — | 850.00 |
| Total: | 100.00 | 100 | 1000 grams |

The procedure for this example was the same as that of Example 6 except that the NUTRASWEET was added after the colloidal silica.

The spray dryer was operated with a feed rate of 40 grams per minute and with the air inlet heater set to provide an air outlet temperature of 25°–30° C. The air pressure was 4.8 bar. The yield of spray dried powder was 75.5%.

The product was a fine white, free-flowing powder having a sweet taste and a slightly bitter aftertaste. The addition to the feed mixture to the spray dryer of a small amount of one or more flavoring agents such as Cherry #271, Cream #59.200A, chocalate or mocha will improve the taste.

EXAMPLE 8

This example describes the preparation of fast dissolving dosage forms using the spray dried taste-neutral acetaminophen of Example 1 and other ingredients as follows:

| Ingredients | Weight % suspension | Grams in suspension |
|---|---|---|
| Gelatin, BY 19/50 | 4.0 | 4.00 |
| Mannitol, granular | 3.0 | 3.00 |
| Deionized water | 69.30 | 69.30 |
| NUTRASWEET, NF | 1.20 | 1.20 |
| Cherry #271 | 0.40 | 0.40 |
| Cream Flavor #59.200/A | 0.20 | 0.20 |
| Sodium lauryl sulfate | 0.10 | 0.10 |
| Powder, Example 1 | 21.80 | 21.80 |

The procedure for preparing a batch of the above suspension takes place in two stages, i.e. the preparation of the gelatin base and the addition of the pharmaceutical agent.

The gelatin base is prepared by adding to the deionized water at 30° C. and mixing until the gelatin is dissolved. The solution is then cooled to 25° C. and the mannitol, the sodium lauryl sulfate, the sweetener, and the flavors are separately added and dissolved.

The taste-neutral spray dried acetaminophen powder is screened through a 20 mesh screen. The powder is then added to the gelatin solution and further admixed with Lightnin for thirty minutes to form a uniform dispersion.

The freeze dryer employed in this example was a Virtis 25 SRC Model Freeze Drier. The fast dissolving dosage forms were prepared by dosing 500 milligrams of the suspension of acetaminophen into each well in a thermoformed blister tray containing 10 wells per tray. The filled trays were placed in a larger tray containing a dry ice-methanol mixture. When the suspension in the wells was frozen, the samples were placed on the freeze dryer trays at a shelf temperature of −45° C.

When the samples had reached a temperature of −45° C., as determined by a probe in a well, the condenser was turned on and the freezer turned off. The condenser temperature was brought to between −40° and −45° C. and the vacuum was turned on to between 50 and 60 millitorrs. The heater was then turned on and the shelf temperature was adjusted to 50°–55° C. The heat-dry cycle lasted for 4 hours. The vacuum, the condenser and the heater were turned off and the samples removed. The wafers from each batch were removed from the wells in the trays. They were white in color and each weighed about 155 milligrams of which about 80 milligrams was acetaminophen. The wafers from each batch when placed on the tongue exhibited a cherry/cream flavor with a very slight bitter aftertaste. When placed in water at 37° C. the wafers disintegrated in less than ten seconds.

EXAMPLE 9

This example describes the preparation of a chewable tablet using the spray dried taste neutral acetaminophen of Example 1 and other ingredients as follows:

| Ingredients | Weight |
|---|---|
| Powder of Example 1, | 500 mg |
| Aluminum Stearate | 2 mg |
| Sorbitol | q.s. to 700 mg |
| Total | 700 mg |

The powder of Example 1 contained about 74% by weight or 370 mg of acetaminophen. The ingredients were mixed in a suitable mixer and formed into tablets. The tablets when chewed in the mouth had a neutral taste and good mouthfeel. The taste could be improved by incorporation into the tablet of suitable flavoring agents such as a mint flavoring agent.

We claim:

1. A therapeutic taste neutral powder form of spray-dried acetaminophen which consists essentially of, based upon the weight of the powder, about 60% to 76% by weight acetaminophen and about 24% to 40% by weight ethyl cellulose, the powder having been spray dried from a suspension of the acetaminophen in a solution of the ethylcellulose in an organic solvent selective for the ethylcellulose having a solids content of at least about 14% by weight.

2. In a pharmaceutical dosage form for oral administration as a solid, which dosage form can be disintegrated by water within ten seconds, the improvement which comprises incorporating into such dosage form as the pharmaceutical substance a therapeutic taste-neutral powder form of spray-dried acetaminophen which consists essentially of, based upon the weight of the powder, about 60% to 76% by weight acetaminophen and about 24% to 40% by weight of ethyl cellulose, the powder having been spray dried from a suspension of the acetaminophen in a solution of the ethylcellulose in an organic solvent selective for the ethylcellulose having a solids content of at least about 14% by weight.

3. The taste neutral powder of claim 1 wherein the solvent selective for ethyl cellulose is methylene chloride.

4. The taste neutral powder of claim 3 wherein the solids content of the suspension of acetaminophen in the solution of ethyl cellulose in methylene chloride is within the range of about 14% to about 19% by weight.

5. The dosage form of claim 2 wherein the solvent selective for ethyl cellulose is methylene chloride.

6. In a pharmaceutical dosage form for oral administration as a solid chewable taste-neutral tablet containing acetaminophen, the improvement which comprises incorporating into such tablet as the pharmaceutical substance a therapeutic taste-neutral powder form of spray-dried acetaminophen which consists essentially of, based upon the weight of the powder, about 60% to 76% by weight acetaminophen and about 24% to 40% by weight ethyl cellulose, the powder having been spray dried from a suspension of the acetaminophen in a solution of the ethylcellulose in an organic solvent selective for the ethyl cellulose having a solids content of at least about 14% by weight.

* * * * *